United States Patent
Hayashi

(10) Patent No.: US 12,014,827 B2
(45) Date of Patent: Jun. 18, 2024

(54) USING ARTIFICIAL INTELLIGENCE AND BIOMETRIC DATA FOR SERIAL SCREENING EXAMS FOR MEDICAL CONDITIONS

(71) Applicant: Tecumseh Vision, LLC, Pittsburgh, PA (US)

(72) Inventor: James Hayashi, Pittsburgh, PA (US)

(73) Assignee: Tecumseh Vision, LLC, Pittsburgh, PA (US)

( * ) Notice: Subject to any disclaimer, the term of this patent is extended or adjusted under 35 U.S.C. 154(b) by 516 days.

(21) Appl. No.: 17/423,743

(22) PCT Filed: Jan. 16, 2020

(86) PCT No.: PCT/US2020/013826
§ 371 (c)(1),
(2) Date: Jul. 16, 2021

(87) PCT Pub. No.: WO2020/150441
PCT Pub. Date: Jul. 23, 2020

(65) Prior Publication Data
US 2022/0122730 A1    Apr. 21, 2022

Related U.S. Application Data

(60) Provisional application No. 62/793,024, filed on Jan. 16, 2019.

(51) Int. Cl.
*G16H 50/20* (2018.01)
*A61B 3/10* (2006.01)
(Continued)

(52) U.S. Cl.
CPC ............. *G16H 50/20* (2018.01); *A61B 3/102* (2013.01); *A61B 3/1225* (2013.01);
(Continued)

(58) Field of Classification Search
CPC ........ G16H 50/20; G16H 10/60; G16H 40/67; G16H 15/00; G16H 30/40; G16H 30/20;
(Continued)

(56) References Cited

U.S. PATENT DOCUMENTS

| | | | |
|---|---|---|---|
| 11,069,055 B2* | 7/2021 | Rollins | ............... A61B 5/0066 |
| 11,717,443 B2* | 8/2023 | Fu | ....................... A61F 9/00808 |
| | | | 606/5 |

(Continued)

FOREIGN PATENT DOCUMENTS

| | | | | |
|---|---|---|---|---|
| WO | 2018094381 A1 | 5/2018 | | |
| WO | WO-2018094381 A1 * | 5/2018 | ............. A61B 3/102 |

(Continued)

OTHER PUBLICATIONS

Zhang J, Mazlin V, Fei K, Boccara AC, Yuan J, Xiao P. Time-domain full-field optical coherence tomography (TD-FF-OCT) in ophthalmic imaging. Ther Adv Chronic Dis. May 2, 2023;14:20406223231170146. doi: 10.1177/20406223231170146. (Year: 2023).*

(Continued)

*Primary Examiner* — Mia M Thomas
(74) *Attorney, Agent, or Firm* — K&L Gates LLP

(57) ABSTRACT

Computer-implemented systems and methods link time-stamped OCT scan data of a patient's retina in a database to a biometric identifier for the patient. An appropriately trained artificial intelligence (AI) computer system determines whether the patient has an eye disease based on the differences between time-stamped OCT scan data for the patient from different time scans.

27 Claims, 8 Drawing Sheets

(51) Int. Cl.
*A61B 3/12* (2006.01)
*G06T 7/00* (2017.01)
*G06V 40/13* (2022.01)
*G06V 40/19* (2022.01)
*G16H 10/60* (2018.01)
*G16H 40/67* (2018.01)

(52) U.S. Cl.
CPC ............ *G06T 7/0016* (2013.01); *G06V 40/13* (2022.01); *G06V 40/19* (2022.01); *G16H 10/60* (2018.01); *G16H 40/67* (2018.01); *G06T 2207/10101* (2013.01); *G06T 2207/20081* (2013.01); *G06T 2207/30041* (2013.01)

(58) Field of Classification Search
CPC ..... A61B 3/102; A61B 3/1225; G06T 7/0016; G06T 2207/10101; G06T 2207/20081; G06T 2207/30041; G06V 40/13; G06V 40/19; G06V 10/95; G06V 40/1365; G06V 40/197; G06V 2201/031; G06F 18/24; G06N 20/20
See application file for complete search history.

(56) References Cited

U.S. PATENT DOCUMENTS

| | | |
|---|---|---|
| 2004/0080326 A1 | 4/2004 | Topp et al. |
| 2005/0080326 A1* | 4/2005 | Mathew .................. A61B 8/00 600/407 |
| 2011/0299034 A1* | 12/2011 | Walsh .................... A61B 3/132 351/206 |
| 2015/0110348 A1 | 4/2015 | Solanski et al. |
| 2015/0178449 A1* | 6/2015 | Ferry .................... G16H 10/60 705/3 |
| 2015/0265144 A1 | 9/2015 | Burlina et al. |
| 2015/0374549 A1* | 12/2015 | Scott ...................... A61F 9/013 606/5 |
| 2016/0015471 A1 | 1/2016 | Piron et al. |
| 2016/0220129 A1* | 8/2016 | Ostroverkhov ...... A61B 5/0261 |
| 2017/0169565 A1* | 6/2017 | Huang ................. A61B 3/1225 |
| 2018/0299658 A1* | 10/2018 | Carrasco-Zevallos ....................... A61B 3/102 |
| 2019/0005684 A1 | 1/2019 | De Fauw et al. |
| 2019/0021908 A1* | 1/2019 | Scott ...................... A61F 9/013 |
| 2019/0110753 A1* | 4/2019 | Zhang .................... G16H 50/20 |
| 2020/0160057 A1* | 5/2020 | Roxas ...................... G06F 3/167 |
| 2021/0081692 A1* | 3/2021 | Vemury ................. G06V 40/10 |
| 2021/0386285 A1* | 12/2021 | Walsh ................. A61B 5/0066 |
| 2023/0344636 A1* | 10/2023 | Chang .................... G16H 15/00 |

FOREIGN PATENT DOCUMENTS

| | | | |
|---|---|---|---|
| WO | 2020150441 A1 | 7/2020 | |
| WO | WO-2020150441 A1 * | 7/2020 | ............. A61B 3/102 |

OTHER PUBLICATIONS

Samples JR, Ahmed II, editors. Current developments in glaucoma surgery and MIGS. Kugler Publications; Jan. 2, 2020. (Year: 2020).*
International Search Report and Written Opinion for International PCT Application No. PCT/US2020/013826, dated Apr. 1, 2020.

* cited by examiner

| Biometric Identifier | Patient ID | Exam Date | Time | OCT Scan Data |
|---|---|---|---|---|
| xxxx | yyyy | 1/10/17 | 10:00:00.00 | Address xyz1 |
| xxxx | yyyy | 1/12/18 | 10:00:00.00 | Address xyz2 |
| xxxx | yyyy | 1/11/19 | 10:00:00.00 | Address xyz3 |
| | | | | |
| | | | | |

FIG. 5

USING ARTIFICIAL INTELLIGENCE AND BIOMETRIC DATA FOR SERIAL SCREENING EXAMS FOR MEDICAL CONDITIONS

PRIORITY CLAIM

The present application claims priority to U.S. provisional patent application Ser. No. 62/793,024, filed Jan. 16, 2019, with the same title and inventor as indicated above, and which is incorporated herein by reference.

BACKGROUND

Glaucoma is an accelerated loss of the nerve fiber layer in the optic nerve. It is estimated that three million Americans have glaucoma, but only half of them are aware of their condition. Worldwide there are more than 60 million people with glaucoma. Great advances have been made in treating glaucoma and other blinding eye diseases, such as diabetic eye disease and age related macular degeneration, but identifying at-risk individuals in an efficient and cost effective manner remains a problem. This problem is further compounded by a worldwide shortage of trained eye care professionals, particularly ophthalmologists (surgeons). An accurate, easily accessed screening mechanism will free ophthalmologists from much of their screening and diagnosing responsibilities to concentrate on treatment. More importantly, the status quo of diagnosing eye diseases has lead to many people in many countries "falling through the cracks."

There is at present no effective way to screen for glaucoma. Using intraocular pressure measurements to screen for glaucoma is very ineffective because many glaucoma patients have normal intraocular pressure, so called "low pressure glaucoma," and even patients with higher pressure will often exhibit normal pressure with a single reading. Compounding this problem is that most people with elevated intraocular pressure do not have glaucoma.

The single most effective measurement for determining if someone has glaucoma is an Ocular Coherence Tomography (OCT) scan of the optic nerve. However, screening for diseases such as glaucoma has always been designed as a single, "one-shot" exam. There are practical reasons for this, but unfortunately some diseases, such as glaucoma, by their very nature make such a "one shot" approach inherently inaccurate with many false positives or false negatives. While a single exam can show if there is extensive damage, a single exam can not convey any information about the rate of loss of the nerve fiber layer in the optic nerve that is indicative of glaucoma. Rather, in a single exam, there will be extensive overlap of normal and glaucomatous optic nerves, whether measuring them by appearance or through more sophisticated analysis such as OCT.

Serial measurements are not a panacea either, however, because there are practical obstacles to serial measurements and comparing previous changes to the OCT exam. The most obvious problem is when a patient changes practice, which often occurs because the patient moved or changed health insurance plans. Even if the patient remained in the same practice, if the practice changed its OCT machine, it may render such comparisons to previous exams on a different machine quite difficult since, unfortunately, the manufacturers of OCT scan equipment themselves often encourage this incompatibility as a form of client retention.

SUMMARY

In one general aspect, the present invention is directed to computer-implemented systems and methods that link time-stamped OCT scan data of a patient's retina in a database to a biometric identifier for the patient. An appropriately trained artificial intelligence (AI) computer system can then determine whether the patient has an eye disease based on the differences between time-stamped OCT scan data for the patient from different time scans. These and other benefits of the present invention will be apparent from the description that follows.

FIGURES

Various embodiments of the present invention are described herein by way of example in connection with the following figures, wherein:

FIG. 5 depicts records of a database according to various embodiments of the present invention;

DESCRIPTION

Figure 1:
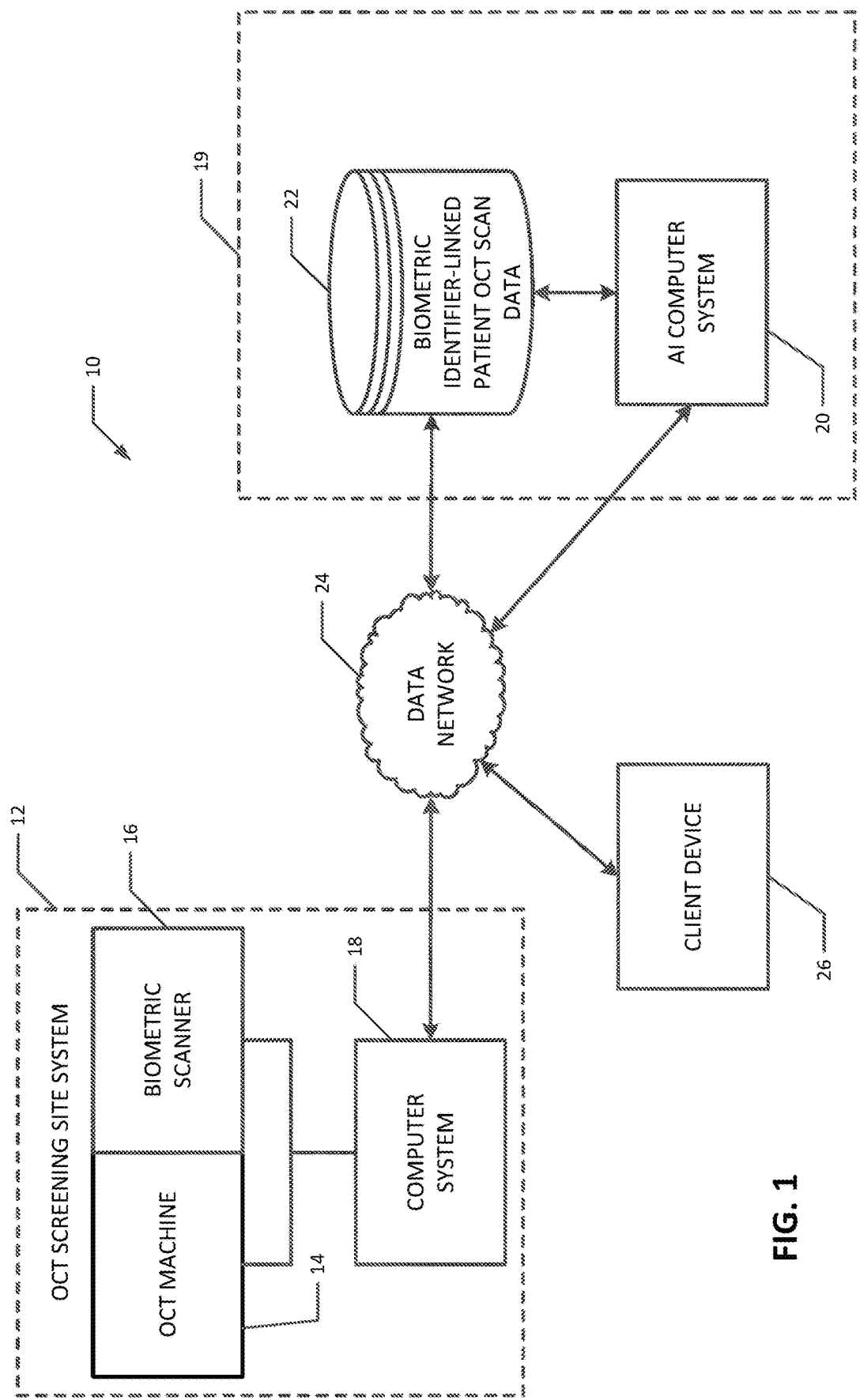
FIGS. 1 and 6 are diagram of systems according to various embodiments of the present invention.

FIG. 1 is a diagram of a system 10 according to various embodiments of the present invention in which a patient has an OCT scan of a body part of the patent performed at a screening site by a screening site system 12. The OCT screening site system comprises an OCT scanner 14 that may be an ocular (or ophthalmic) OCT scanner that generates high-resolution images of the patient's retinas. The screening site system 12 may also comprise a biometric scanner 16 that, as part of the OCT scanning process, scans a biometric identifier for the patient, so that the patient's biometric identifier can be uniquely linked to the patient's OCT scan results from the screening. The biometric scanner 16 may be, for example, a fingerprint scanner, a retina/iris pattern scanner, or any other suitable biometric scanner that uniquely identifies the patient by evaluating one or more distinguishing biometric traits of the patient. Also as shown in FIG. 1, the screening site system 12 may also comprise a local computer system 18 that is in communication with the OCT and biometric scanners 14, 16.

When visiting the screening site, a patient may first identify/verify him/herself through the biometric scanner 16. For example, when the visiting the scanning site, the biometric scanner 16 scan the patient's biometric identifier (e.g., fingerprint, iris, etc.) The biometric scanner 16 captures the patient's biometric identifier, and the biometric scan data are then sent by the local computer system 18 to a remote, back-end computer system 19 that comprises a computer database system 22. The data may be sent to the back-end computer system 19 via a data network 24, which may be the Internet, a LAN, a WAN, etc. The transmitted biometric scan data may be encrypted and/or compressed before transmission to the back-end computer system 19 for storage in the computer database system 22. The computer database system 22 may then look-up the patient in the computer database system 22 based on the biometric identification data in the database to verify the identity of the patient. That is, the computer database system 22 may store patient data that are associated with each unique biometric identifier. The patient data may include, for example, the patient's name, birthdate, social security number or other numerical identifier (e.g., tax ID, etc.), address, and contact information (e.g., email, phone number, mailing address, etc.). The patient data in the computer database system 22 may be encrypted to preserve the identity of the patient. In other embodiments, the patient data may not include any personal identifying information. For example, the patient data may merely include an email address to which the results can be sent. That way, the database system 22 does not include any other personal identifying information that could reveal the identity of the patient. Further, the email address could also be encrypted in the database 22.

When the computer database system 22 receives biometric data from the screening site system 12, the computer database system 22 determines whether there is match of the biometric identifier to any of the records in the database 22. If so, the patient's identity is verified such that the OCT scan data for the patient as part of the imminent scan (described below) can be linked to the patient.

If the patient is not in the computer database system 22, for example if it is the patient's first visit to the screening site or a related one, the computer system 18 may prompt the patient to input the identifying patient data, such as the patient's name, birthdate, social security number or other numerical identifier (e.g., tax ID, etc.), address, and contact information (e.g., email, phone number, mailing address, etc.). In embodiments where just an email address is stored, the computer system 18 may prompt the patient to input the email address to which the results should be sent. The patient data may then be transmitted to and stored in the remote computer database system 22. Thus, the remote computer database system 22 may associate the biometric identification of the patient with the (preferably encrypted) patient data.

Figure 2:
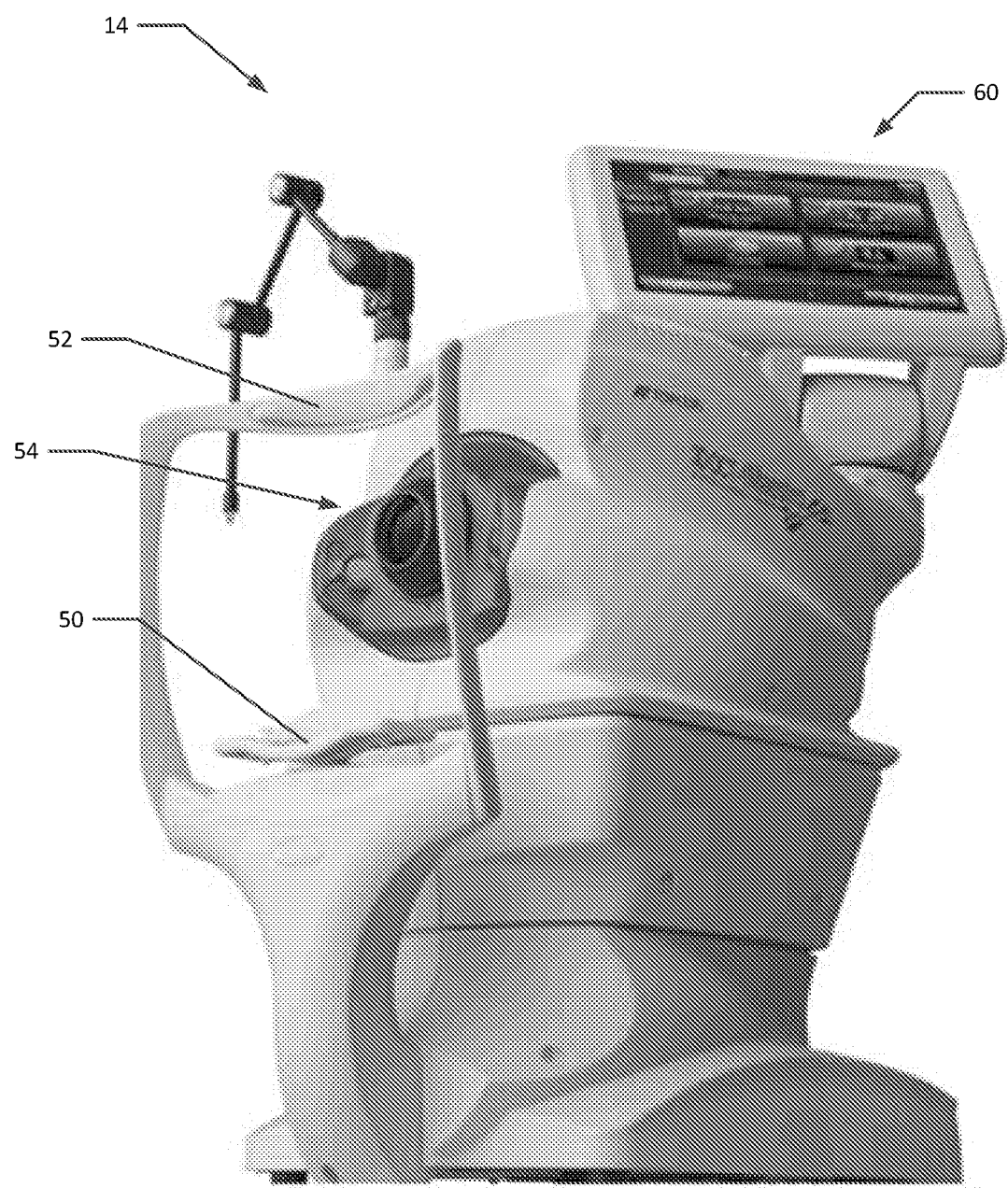
FIG. 2 depicts an OCT machine.

After identifying him/herself with the biometric scanner 16 (and entering identifying information if necessary), the patient may then complete the OCT screening. FIG. 2 depicts a typical OCT scan machine 14. The patient sits in front of the machine with his/her chin on the chin rest 50 and their forehead on the forehead rest 52 with one of their eyes in front of the lens 54. The screen of the computer device 18 (e.g., screen 60 in FIG. 2) and/or a loudspeaker thereof can instruct the patient to do particular eye first (e.g., right eye), followed by the other (e.g., left). The OCT scanner 14 than scans the patient's eyes.

Figure 3:
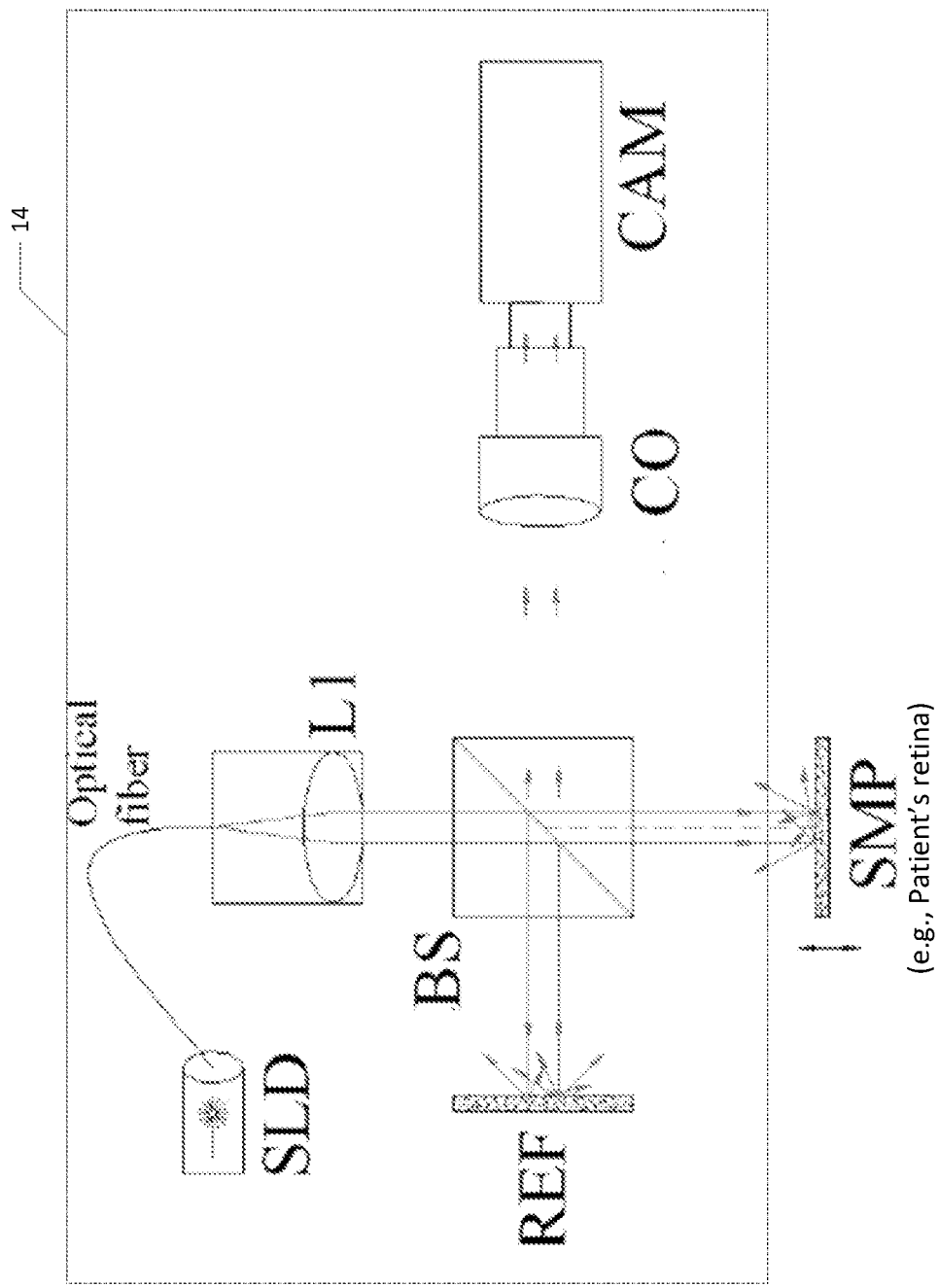
FIG. 3 is a block diagram of an OCT machine.
Figure 4A:
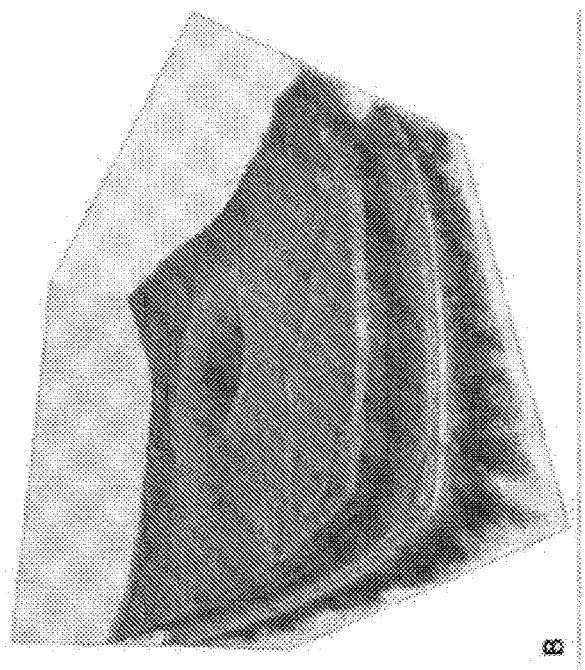
FIG. 4A shows a Fourier-domain optical coherence tomography (FD-OCT) B-scan of the fovea of a sample patient.
Figure 4B:
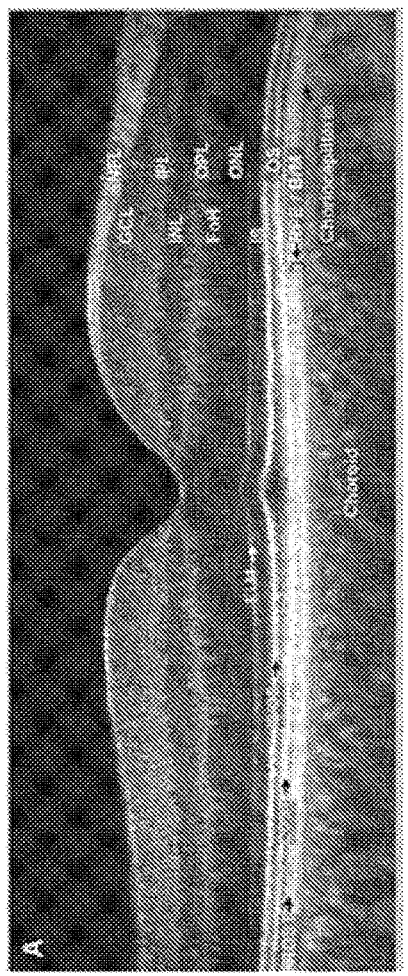
FIG. 4B shows a volumetric reconstruction of the central foveal region from 100 B-scans from the same patient as for FIG. 4A.

The OCT scanner 14 is a medical imaging device that uses light (usually infrared light) to capture micrometer-resolution, three-dimensional images from within optical scattering media (e.g., biological tissue), such as the patient's retina. The OCT scanner 14 may include an interferometer (e.g., a Michelson type) with a low coherence, broad bandwidth light source, such as a super-luminescent diode (SLD) or laser. FIG. 3 is a block diagram of one possible type of OCT scanner 14 according to various embodiments of the present invention. Light from the light source, e.g., the SLD, is projected through a convex lens LI, and then split into two beams by a beam-splitter (BS). One beam is directed to a reference (REF) and the other beam is directed to the sample (SMP), e.g., the patient's retina. The reflected light from the sample and reference paths are recombined. A light detector, such as a camera (CAM in FIG. 3) or photodetector, collects the images data for digital processing. FIGS. 4A-B provide examples of an OCT scan of a retina. The OCT scanner 14 preferably captures high-resolution 3D-OCT imaging of the retina. FIG. 4A shows a Fourier-domain optical coherence tomography (FD-OCT) B-scan of the fovea of a sample patient and FIG. 4B shows a volumetric reconstruction of the central foveal region from 100 B-scans from the same patient.

After the scanning, the scan retina image data (or other body part, depending on what the types of diseases being diagnosed) collected by the OCT scanner 14 from the patient is transmitted by the local computer system 18, via the data network 24, to the computer database system 22, where the OCT scan data are stored. The OCT data are stored in the database 22 so that they are associated with the patent's biometric identifier, as described below. In various embodiments, the local computer system 18 may encrypt and/or compress the scan data before transmission to the computer database system 22.

FIG. 5 is a table that illustrates the type of data that may be stored in the database 22 and how the data are associated. The example table shown in FIG. 5 shows three OCT scans performed for one patient. Each scan is represented by a row in the database, whose fields include: a field for the patient's biometric identifier; a field for the patient's ID number; a field for the date and time of the exam; and a field(s) for the OCT scan data for the right and left eyes of the patient. Patent data about the patient can also be stored in the records, or another database in the database computer system 22 can associated each patient ID to the patient's personal data. In various embodiments, the OCT scan data may be relatively large files. As such, the OCT scan data field(s) in the table may include address locations in the database where the time-stamped OCT scan data for the exam are stored. The illustrated example of FIG. 5 shows three different scans for a single patient, identified by a common biometric identifier and all having the same patient ID. The OCT scans were performed roughly a year apart each time (January of 2017, 2018 and 2019 respectively in this example), with the OCT scan data for each separate scan being stored at different addresses.

In various embodiments, the OCT scanner 14, the biometric scanner 16, and the local computer system 18 may be separate devices that are in communication via a suitable data bus; or they may be integrated into one or two discrete devices. Also, the OCT scan machine 14 may be a self-service machine where the patient can perform the scan by him/herself, or there could an attendant at the screening site to assist the patient perform the scan. In some embodiments, no pupil-dilating eye drops are used. In other embodiments, the patient or an attendant at the screening site may dilate the patient's pupils prior to the OCT scan with pupil-dilating eye drops. Also, both the OCT scanner 14 and the biometric scanner 16 could be integrated into a single, self-service scanning unit. A monitor on the scanning unit may provide visual instructions to a patient on how to perform the biometric and OCT scans using the scanning unit. The local computer could also be included in the scanning unit and connected to (in data communication with) the OCT scanner 14 and the biometric scanner 16.

Figure 6:
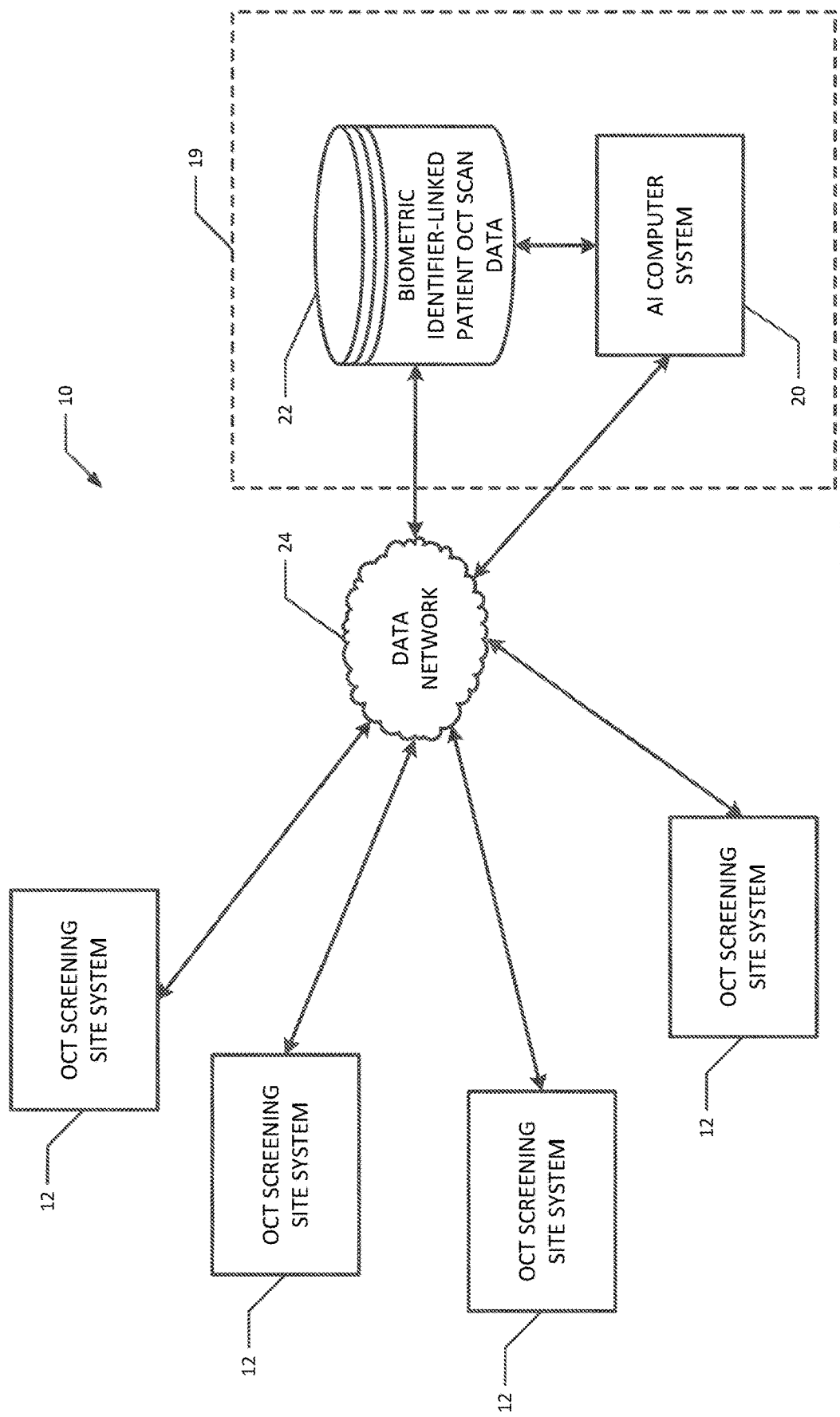

Preferably, as shown in FIG. 6, there are multiple screening site systems 12 set up at disparate locations, which all upload their captured, biometrically-linked OCT scan data to the computer database system 22. That way, a patient could visit any of the screening site systems 12 to have an OCT scan, and the computer database system 22 will link the patient's OCT scan to the patent because of the patient's biometric identifier, despite the fact that the patient was tested at disparate locations. Some or all of the screening site systems 12 could be located in walk-up, easy-to-access, appointment-free locations, such as pharmacies, retail stores, etc., and they could also be located in places that require appointments, such as doctors' offices, clinics, etc. That way, a patient could go to one screening site location on one day to have the OCT exam performed, and then go to another screening site location on another day (e.g., a month later, a year later, etc.) to have a second OCT exam performed, and so on. Also, some or all of the screening site systems 12 could be located in doctor's offices, clinics, hospitals, etc. No matter the location where the screening was performed, the time-stamped OCT scan data for the patient are stored in the computer database system 22 and linked to the patient because of the patient's biometric identifier. Any or all of the screening sites could also be equipped with an autorefractor for determining a corrective lens prescription for the patient.

Referring to FIGS. 1 and 6, the system 10 may further comprise an AI computer system 20. In various embodiments, the AI computer system 20 is trained, through machine learning, to classify eye diseases in a patient based on differences (or the "delta") between time-variant OCT scans of the patient's retinas. That is, the AI computer system 20 may compute, based on the delta between time-variant OCT scans for the patient, a likelihood that the patient has various eye diseases and related conditions (e.g. a classification that the likelihood is above or below certain levels). The eye diseases that the AI computer system 20 may be trained to classify include, for example, glaucoma, whether the patient has rapidly or slowly progressing age-related, wet and/or dry, macular degeneration (ARMD) or diabetic retinopathy (DR). The AI computer system 20 could also be combined with an AI-based system that diagnoses such eye-related diseases from a single OCT scan, such as described in published PCT application WO/2018/094381, entitled "System and Method for Automatic Assessment of Disease Condition Using OCT Scan Data," by J. Hayashi et al, which is incorporated herein by reference in its entirety.

Figure 7:
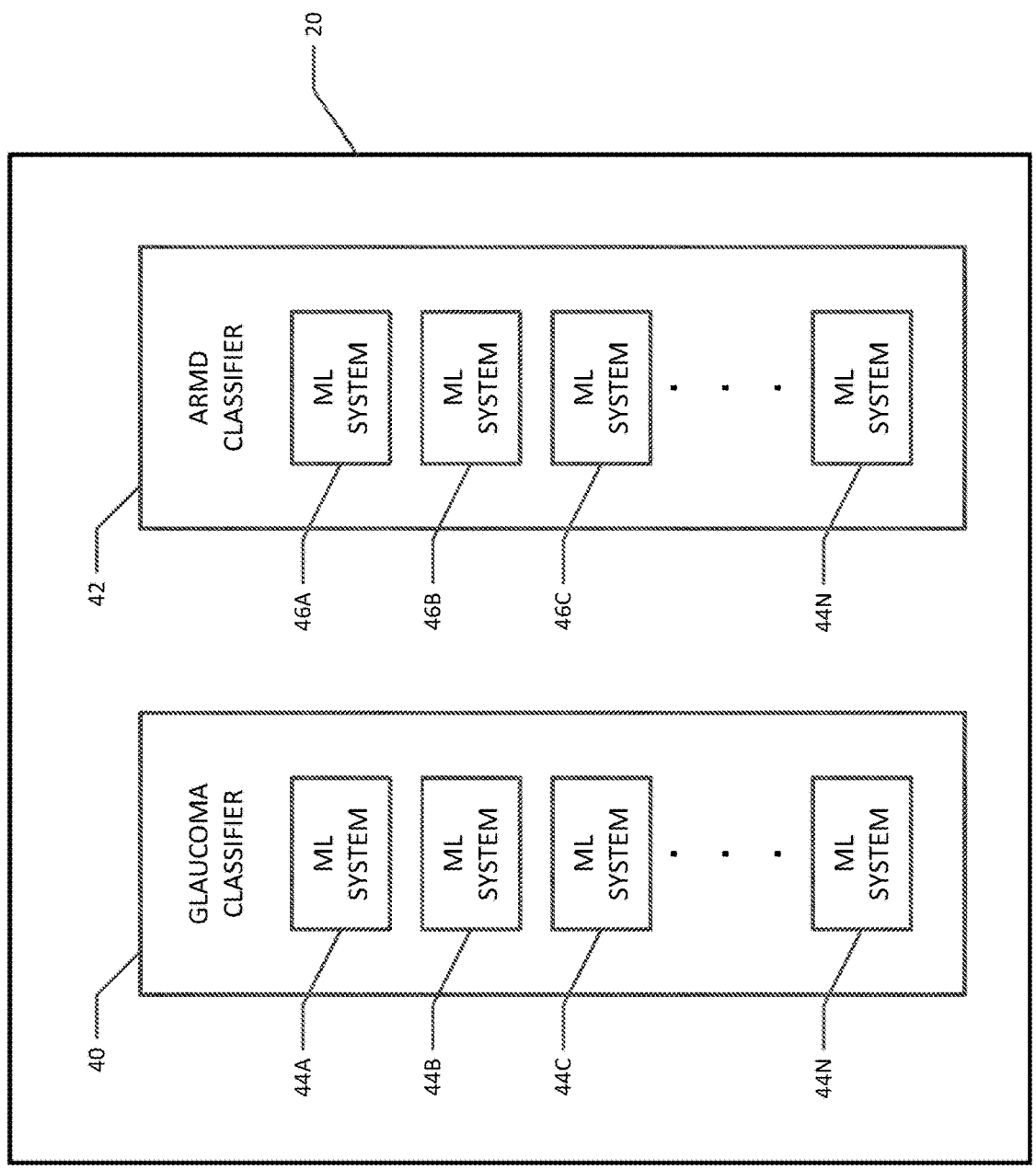
FIG. 7 depicts an AI computer system according to various embodiments of the present invention.

FIG. 7 illustrates an example of the AI computer system 20 with classifiers for glaucoma 40 and ARMD 42 (e.g., whether dry ARMD is progressing rapidly). Of course, in other embodiments, the AI computer system 20 could comprise fewer or additional classifiers as described above. Each classifier 40, 42 may comprise one or more machine-learning systems 44A-N, 46A-N. Where a classifier 40, 42 comprises multiple machine-learning systems 44A-N, 46A-N, the machine-learning systems 44A-N, 46A-N could be part of an ensemble. That is, for example, in an ensemble, is ensemble member is trained to have a different machine learning model, and the output of the ensemble members are averaged in some manner to generate a final output for the ensemble/classifier.

Each of the machine-learning systems 44A-N, 46A-N may use any suitable machine-learning modeling technique that is suitable for the classification task. For example, some or all of the machine learning systems 44A-N, 46A-N may comprise artificial neural networks, including deep neural networks, decision trees, support vector machines, clustering, and/or rule-based machine learning. Where deep neural networks are used, the deep neural networks could comprise convolutional neural networks, recursive neural networks, recurrent neural networks, and/or feedforward neural networks.

No matter the types of machine learning systems that are used, the machine learning systems need to be trained prior to classifying a patient based on the time-variant OCT scans of the patient. In the training process, the statistical models for the machine learning systems 44A-N, 46A-N may be generated from a database or library of OCT scan image training data, which has OCT scan image training data from different exams times for the test subjects. That way, the machine learning systems 44A-N, 46A-N can be trained on the differences (or deltas) between OCT scans from different times. For example, to generate a machine learning system 44A-N for glaucoma, there should be sufficient and sufficiently distributed amounts of training data (deltas in OCT scans) in the database/library where the test subjects are known to both have and not have glaucoma. From the positive and negative samples, the machine learning system 44A-N can train each of its one or more statistical models to classify, once trained, whether a particular OCT scan delta for patient should be classified as indicating that the patient has glaucoma (or more particularly, the machine learning system 44A can compute the likelihood that the patient has glaucoma based on its statistical model(s)). Similarly, the machine-learning systems 46A-N for ARMD may be trained, based on the OCT scan deltas, to determine whether the patient is likely have rapidly progressing ARMD (e.g., dry MD) based on the patient's OCT scan delta.

Figure 8:
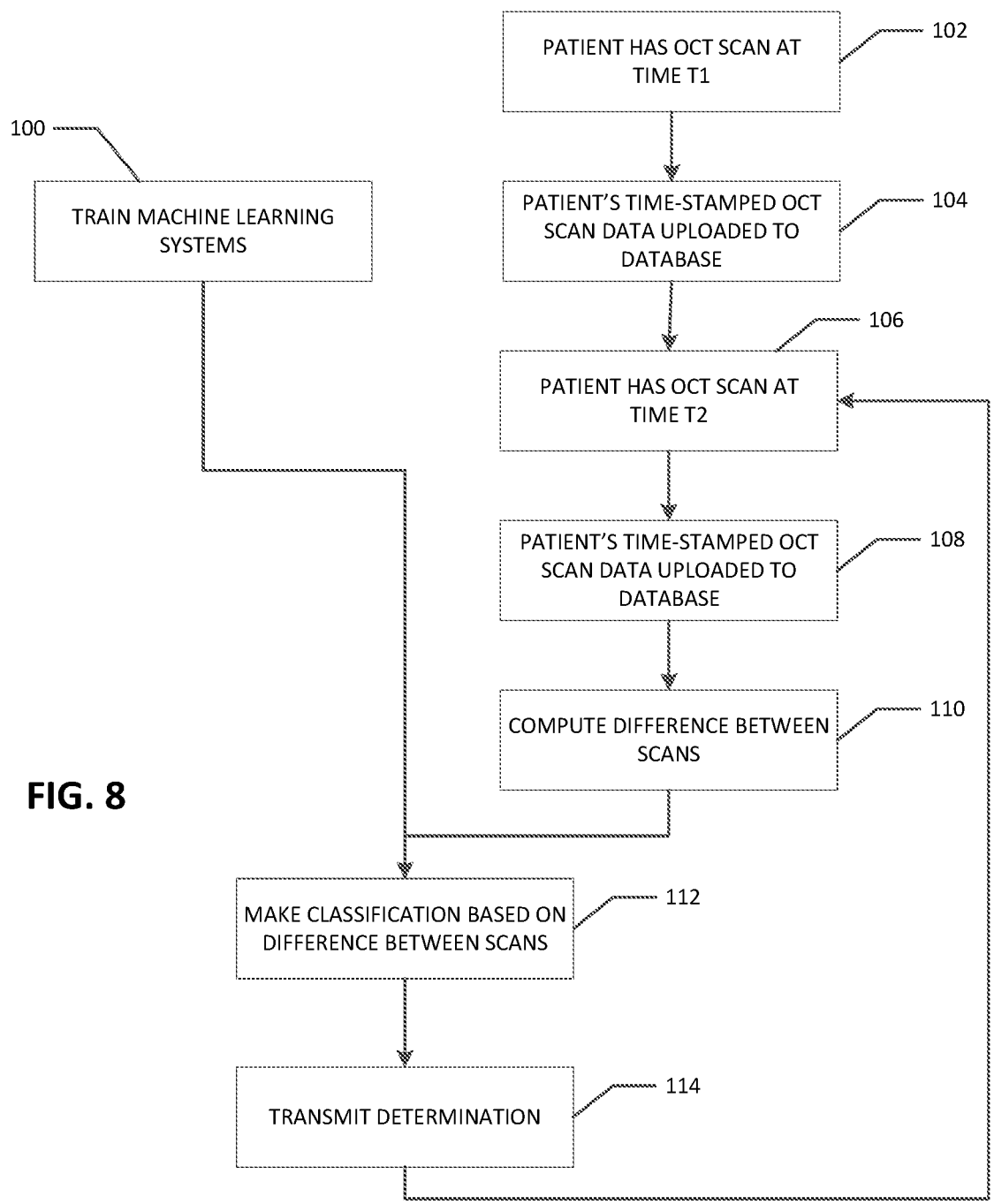
FIG. 8 depicts a method performed by the systems of FIGS. 1 and/or 6 according to various embodiments of the present invention.

FIG. 8 is a flow chart of a process, according to various embodiments of the present invention, that involves the computer system 10. At step 100, the machine learning system(s) 44A-N, 46A-N for the classifier(s) 40, 42 of the AI computer system 20 are trained. At step 102, a patient goes to a screening site system at a location to have an OCT scan performed (at time T1). Associated with that scan, the patient's time-stamped OCT scan data are uploaded at step 104 from the screening site system 12 to the computer database system 22 and linked to the patient by the patient's biometric identifier, as collected at the screening site system 12.

Then, at step 106, at a later time (T2), the patient has another OCT scan performed. The patient can have the second OCT scan performed at the same screening site location as the prior scan (at step 102) or at a different site (see FIG. 6). The results from the second screening are then uploaded at step 108 to the computer database system 22. Again, the scan data from both the first and second scans will be linked to the patient in the computer database system 22 because of the patient's biometric verification at the screening time and location.

Then, at step 110, the AI computer system 20 may compute the delta between the first and second scans for the patient (e.g., the difference between the scan at time T1 and the scan at time T2). Then, at step 112, the already-trained machine learning model(s) of the AI computer system 20 can make a classification for the patient based on the differences between the two time-variant scans for the patient. For example, the delta between the patient's time-variant OCT scan can be input to the glaucoma classifier 40, which may then compute a likelihood that the patient has glaucoma based on the statistically trained model for the glaucoma classifier trained at step 100. The AI computer system 20 may have one or many such machine learning systems as described above, such as machine learning systems for glaucoma, ARMD, DR, etc. The AI computer system 20 may input the delta between the patient's time-variant OCT scan into each such machine learning system to get a classification for each (e.g., a classification for glaucoma, ARMD, DR, etc.) or the AI computer system 20 may compute the classification for a proper subset of its machine-learning systems. At step 114, the AI computer system 20 may then transmit data or a file to a client device 26 (see FIG. 1) via the network 24, wherein the transmitted data/file that has the output or determination of the AI computer system's analysis (or a HTTP link thereto). The client device 26 may be, for example, a device (e.g., a smartphone, PC, tablet, laptop, etc.) of the patient and/or a caregiver for the patient. The address to which the output should be sent may be stored in the computer database system 22 and specified in the patient's profile contact information. The output that is sent to the patient may include determinations for each classifier and/or a message to see an eye doctor immediately (or not if there is little likelihood for any of the screened-for eye diseases). For example, if the AI computer system 20 determines that the patient is likely to have one of the screened-for eye diseases, the message sent to the patient may be to see a trained eye doctor soon.

Steps 106-114 could be performed essentially in real-time. That is, for example, while the patient is at the screening site, steps 106-114 could be performed so that the patient receives the determination while at the screening site. Alternatively, the analysis (e.g., steps 108-112) could be performed after the screening so that the results are sent at some time (e.g., one or more days) after the conclusion of the screening. Thus, one apparent benefit from benefits of the present invention is that is accelerates the time for a patient to see a doctor. For example, presently, a patient has to schedule the OCT scan, which could be a several-month wait, and they wait for a follow-up appointment, which could be another several-month wait. With embodiments of the present invention, for example, the patient could go to any screening site at a convenient time, and get the results in real-time or otherwise very quickly. Then, if needed, the patient could schedule an appointment with an eye doctor on the basis of the results from the AI computer system, thereby accelerating the time for the patient to get treatment, which can be critical since urgent treatment in many cases can lead to a more favorable outcome for the patient.

In embodiments where the AI computer system has classifiers for multiple eye diseases, the patient, at the OCT screening site, could select which of the available classifiers to use. For example, one patient may want all of the available classifiers used and, as such, at the OCT screening site, that patient may select a menu option that is for all of the available classifiers to be used. Another patient, however, may only want a subset of the classifications performed. In such a scenario, that patent could pick, at the OCT scanning site, which ones to use (e.g., glaucoma only) from a list of available options.

The process of FIG. 8 can be repeated the next time the patient has his/her eyes scanned by one of the OCT screening system systems 12. This is shown by the feedback loop from step 114 to 106, except that the next screening will be at time T3 and two deltas can be computed: T1 vs. T3 and T2 vs. T3. The AI computer system 20 may make a single classification for each tested-for conditions (e.g., glaucoma, ARMD, etc.) by combining in some manner the results for each of the two deltas. The process can be repeated for fourth, fifth and sixth scans, and so on.

In the above-described embodiments, the AI computer system 20 comprised numerous eye-disease classifiers and each one was used to classify a patient when the patient had a new OCT scan. In various embodiments, the patient could select which diseases to test for instead of having all of them checked. For example, via a user interface at the screening site, the patient could select to just have one or a couple diseases checked for, at the patient's option, instead of all of the possible diseases that could be checked by the AI computer system 20.

The back-end computer system 19 and the computer database system 22 may comprise a database and a database management system (DBMS). In various embodiments, the back-end computer system 19 may be implemented with one or a number of networked computer servers. Also, the computer database system may be implemented with one or a number of networked database servers. The database servers could comprise a federated database system wherein multiple constituent databases are interconnected via a computer network and may be geographically decentralized.

The AI computer system 20 is implemented with computer hardware and software. For example, the AI computer system 20 could be part of an integrated computer system (e.g., a server or network of servers) that has multiple processing CPU cores. One set of cores could execute the program instructions for one machine learning system 44A, another set for another machine learning system 44B, and so on. The program instructions could be stored in computer memory that is accessible by the processing cores of the AI computer system 20, such as RAM, ROM, processor registers or processor cache, for example. The program instructions could also be stored in computer memory utilized as backup storage for inactive machine learning systems, such as secondary computer memory, such as hard drives. In other embodiments, some or all of the machine learning systems could execute on graphical processing unit (GPU) cores or processing cores of an AI accelerator. For example, the cores could be part of a general-purpose GPU (GPGPU) pipeline. GPU cores operate in parallel and, hence, can typically process data more efficiently that a collection of CPU cores, but all the cores execute the same code at one time. Thus, if the machine learning systems within one AI computer system 20 were implemented with a GPGPU pipeline, the GPU cores would need to take turns executing the code for each system. An AI accelerator is a class of processor designed to accelerate AI tasks, such as training deep networks. AI accelerators often have tens of thousands of cores (e.g., 65,000 cores) and operate on lower-precision arithmetic (e.g., 8-bit precision).

Also, the AI computer system 20 may be part of a distributed computer system. For example, the computer devices (e.g., servers) that implement the AI computer system 20 may be remote from each other and interconnected by data networks, such as a LAN, WAN, the Internet, etc., using suitable wired and/or wireless data communication links. Data may be shared between the various systems using suitable data links, such as data buses (preferably high-speed data buses) or network links (e.g., Ethernet).

The software for the various machine learning systems (e.g., machine learning systems 44A-N, 46A-N) and other computer functions described herein may be implemented in computer software using any suitable computer programming language such as .NET, C, C++, Python, and using conventional, functional, or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high level languages include Ada, BASIC, C, C++, C#, COBOL, Fortran, Java, Lisp, Pascal, Object Pascal, Haskell, ML; and examples of scripting languages include Bourne script, JavaScript, Python, Ruby, Lua, PHP, and Perl.

In addition, the concept of linking patient data to a biometric identifier for the patient can be used for other types of patient data besides OCT scan data. For example, the computer database system 22 (or a similarly configured database) could link a patient's biometric identifier to other types of patient data, such test results for sexually transmitted diseases (STDs) and/or genetic testing.

In one general aspect, therefore, the present invention is directed to a system comprising (i) a back-end computer system 19 that comprises a computer database system 22 and (ii) a plurality of distributed OCT scanning systems 12. Each OCT scanning system 12 comprises: an OCT scanner 14 for generating OCT scan data of a patient; a biometric scanner 16 for generating a biometric scan data of the patient; and a local computer 18 that is in communication with the back-end computer system 19, the OCT scanner 14 and the biometric scanner 16. The local computer 18 for each of the plurality of distributed OCT scanning systems 12 is configured to transmit time-stamped OCT scan data and the biometric scan data for a patient to the back-end computer system 19. The back-end computer system 19 is configured to store the time-stamped OCT scan data for the patient in the computer database system 22 such that the time-stamped OCT scan data for the patient are linked to the biometric scan data for the patient.

In another general aspect, the present invention is directed to a method that comprises receiving, by a back-end computer system 19, from a first OCT scanning system 12 that is one of a plurality of distributed OCT scanning systems, biometric scan data and first, time-stamped OCT scan data for a patient, where the biometric scan data and the first, time-stamped OCT scan data are captured by the first OCT scanning system 12. The method also comprises searching, by the back-end computer system 19, a computer database system 22 of the back-end computer system 19 for a match for the patient's biometric scan data. The method further comprises, upon finding a match for the patient's biometric scan data, storing, by the back-end computer system 19 in the computer database system 22 of the back-end computer system 19, the patient's first, time-stamped OCT scan data such that the first, time-stamped OCT scan data for the patient are linked to the biometric scan data for the patient.

In various implementations, the back-end computer system 19 is further configured to perform a machine-learning classification on differences between first OCT scan data for the patient and second OCT scan data for the patient, where the first and second OCT scan data have different time stamps. For example, the OCT scanners 14 of the plurality of distributed OCT scanning systems 12 may be for OCT scanning a patient's retinas, in which case the machine-learning classification by the back-end computer system 19 can be configured to make a diagnosis of an eye disease (such as glaucoma, ARMD, diabetic retinopathy) for the patient based on the differences between the first OCT scan data for the patient and the second OCT scan data for the patient. The second OCT scan data may be collected at the same OCT scanning system as the first OCT scan data or at a second, different, geographically separate OCT scanning system from the first OCT scanning system.

In any of the above-described implementations, the biometric scanner 16 could be a fingerprint scanner or an iris scanner, in which case the biometric scan data would be fingerprint or iris scan data, as the case may be. Also, the biometric scanner and the OCT scanner of the distributed OCT scanning systems 12 may be integrated in a single, self-service scanning unit.

In various implementations, the local computer is configured not to transmit a name, a mailing address, a birthday, and a social security number for the patient to the back-end computer system. Also, the back-end computer system may be configured not to link the patient's name, mailing address, birthday and social security number to the biometric scan data for the patient. Also, the local computer system may be configured to encrypt the time-stamped OCT scan data and the biometric scan data for the patient prior to transmitting the time-stamped OCT scan data and the biometric scan data for the patient to the back-end computer system.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. Further, it is to be understood that the figures and descriptions of the present invention have been simplified to illustrate elements that are relevant for a clear understanding of the present invention, while eliminating, for purposes of clarity, other elements. While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

What is claimed is:

1. A system comprising:
   a back-end computer system that comprises a computer database system; and
   a plurality of distributed OCT scanning systems, wherein each OCT scanning system comprises:
   an OCT scanner for generating OCT scan data of a patient;
   a biometric scanner for generating a biometric scan data of the patient; and
   a local computer that is in communication with the back-end computer system, the OCT scanner and the biometric scanner,
   wherein:
   the local computer for each of the plurality of distributed OCT scanning systems is configured to transmit time-stamped OCT scan data and the biometric scan data for a patient to the back-end computer system; and
   the back-end computer system is configured to store the time-stamped OCT scan data for the patient in the computer database system such that the time-stamped OCT scan data for the patient are linked to the biometric scan data for the patient.

2. The system of claim 1, wherein the back-end computer system is further configured to perform a machine-learning classification on differences between first OCT scan data for the patient and second OCT scan data for the patient, where the first and second OCT scan data have different time stamps.

3. The system of claim 2, wherein:
   the OCT scanners of the plurality of distributed OCT scanning systems are for OCT scanning a patient's retinas; and
   the machine-learning classification by the back-end computer system is configured to make a diagnosis of an eye disease for the patient based on the differences between the first OCT scan data for the patient and the second OCT scan data for the patient.

4. The system of claim 3, wherein the eye disease comprises glaucoma.

5. The system of claim 3, wherein the eye disease comprises ARMD.

6. The system of claim 3, wherein the eye disease comprises diabetic retinopathy.

7. The system of claim 1, wherein the biometric scanner comprises a fingerprint scanner.

8. The system of claim 1, wherein the biometric scanner comprises an iris scanner.

9. The system of claim 1, wherein the biometric scanner and the OCT scanner of the distributed OCT scanning systems are integrated in a single, self-service scanning unit.

10. The system of claim 1, wherein:
the local computer is configured not to transmit a name, a mailing address, a birthday, and a social security number for the patient to the back-end computer system; and
the back-end computer system is configured not to link the patient's name, mailing address, birthday and social security number to the biometric scan data for the patient.

11. The system of claim 1, wherein the local computer system is configured to encrypt the time-stamped OCT scan data and the biometric scan data for the patient prior to transmitting the time-stamped OCT scan data and the biometric scan data for the patient to the back-end computer system.

12. A method comprising:
receiving, by a back-end computer system, from a first OCT scanning system that is one of a plurality of distributed OCT scanning systems, biometric scan data and first, time-stamped OCT scan data for a patient, wherein the biometric scan data and the first, time-stamped OCT scan data are captured by the first OCT scanning system;
searching, by the back-end computer system, a computer database system of the back-end computer system for a match for the patient's biometric scan data;
upon finding a match for the patient's biometric scan data, storing, by the back-end computer system in the computer database system of the back-end computer system, the patient's first, time-stamped OCT scan data such that the first, time-stamped OCT scan data for the patient are linked to the biometric scan data for the patient.

13. The method of claim 12, further comprising receiving and storing, by the back-end computer system in the computer database system, second, time-stamped OCT data for the patient, such that the second, time-stamped OCT data for the patient are linked to the biometric scan data for the patient, and wherein the first, time-stamped OCT data for the patient are collected at a different time than the second, time-stamped OCT data.

14. The method of claim 13, wherein receiving the second, time-stamped OCT data for the patient comprises receiving, by the back-end computer system, the second, time-stamped OCT data for the patient from a second OCT scanning system that is one of the plurality of distributed OCT scanning systems and geographically separate from the first OCT scanning system.

15. The method of claim 13, wherein receiving the second, time-stamped OCT data for the patient comprises receiving, by the back-end computer system, the second, time-stamped OCT data for the patient from the first OCT scanning system.

16. The method of claim 13, further comprising performing, by the back-end computer system, a machine-learning classification on differences between the first, time-stamped OCT scan data for the patient and second, time-stamped OCT scan data for the patient.

17. The method of claim 16, wherein:
the OCT scanners of the plurality of distributed OCT scanning systems are for OCT scanning a patient's retinas; and
the machine-learning classification performed by the back-end computer system is configured to diagnose an eye disease for the patient based on the differences between the first, time-stamped OCT scan data for the patient and second, time-stamped OCT scan data for the patient.

18. The method of claim 17, wherein the eye disease comprises glaucoma.

19. The method of claim 17, wherein the eye disease comprises ARMD.

20. The method of claim 17, wherein the eye disease comprises diabetic retinopathy.

21. The method claim 17, wherein:
the method further comprises receiving, by the back-end computer system, a selection by the patient of the eye disease to make a diagnosis for from the differences between the first, time-stamped OCT scan data for the patient and second, time-stamped OCT scan data for the patient; and
performing the machine-learning classification comprises performing, by the back-end computer system, the machine-learning classification on the differences between the first, time-stamped OCT scan data for the patient and the second, time-stamped OCT scan data for the patient to the make a diagnosis of the eye disease selected by patient.

22. The method of claim 12, wherein the biometric scan data comprise fingerprint scan data of the patient.

23. The method of claim 12, wherein the biometric scan data comprise iris scan data of the patient.

24. The method of claim 12, wherein receiving the biometric scan data and the first, time-stamped OCT scan data for the patient comprises receiving, by the back-end computer system, from the first OCT scanning system, encrypted biometric scan data and encrypted first, time-stamped OCT scan data for the patient.

25. The method of claim 12, further comprising:
receiving, by the back-end computer system, non-OCT scan test data for the patient; and
storing, by the back-end computer system in the computer database system, the non-OCT scan test data for the patient such that the non-OCT scan test data for the patient is linked to the patient's biometric scan data.

26. The method of claim 25, wherein the non-OCT scan test data for the patient comprises genetic test data for the patient.

27. The method of claim 25, wherein the non-OCT scan test data for the patient comprises STD test data for the patient.

* * * * *